(12) United States Patent
Liang et al.

(10) Patent No.: US 11,992,549 B2
(45) Date of Patent: May 28, 2024

(54) OIL-IN-WATER EMULSION

(71) Applicant: Wacker Chemie AG, Munich (DE)

(72) Inventors: Xinyu Liang, Shanghai (CN); Zhiyuan Xu, Shanghai (CN)

(73) Assignee: Wacker Chemie AG, Munich (DE)

( * ) Notice: Subject to any disclaimer, the term of this patent is extended or adjusted under 35 U.S.C. 154(b) by 440 days.

(21) Appl. No.: 17/250,923

(22) PCT Filed: Sep. 27, 2018

(86) PCT No.: PCT/CN2018/107847
§ 371 (c)(1),
(2) Date: Mar. 27, 2021

(87) PCT Pub. No.: WO2020/061880
PCT Pub. Date: Apr. 2, 2020

(65) Prior Publication Data
US 2022/0008320 A1    Jan. 13, 2022

(51) Int. Cl.
| A61K 8/898 | (2006.01) |
| A61K 8/06 | (2006.01) |
| A61K 8/891 | (2006.01) |
| A61K 8/92 | (2006.01) |
| A61Q 5/00 | (2006.01) |
| A61Q 19/00 | (2006.01) |

(52) U.S. Cl.
CPC .............. *A61K 8/898* (2013.01); *A61K 8/062* (2013.01); *A61K 8/891* (2013.01); *A61K 8/922* (2013.01); *A61Q 5/00* (2013.01); *A61Q 19/00* (2013.01)

(58) Field of Classification Search
CPC . A61K 8/41; A61K 8/898; A61K 8/06; A61Q 5/12
USPC .......................................... 424/70.12, 70.122
See application file for complete search history.

(56) References Cited

FOREIGN PATENT DOCUMENTS

| CA | 2721607 A1 | 10/2009 |
| CN | 104000749 A | 8/2014 |
| CN | 106109270 A | 11/2016 |
| EP | 0160430 A2 | 6/1985 |
| FR | 2761599 A1 | 10/1998 |
| FR | 2887450 A1 | 12/2006 |
| JP | 2012240915 A | 12/2012 |
| WO | 2007133720 A2 | 11/2007 |
| WO | 2009017866 A1 | 2/2009 |
| WO | 2015082358 A1 | 6/2015 |
| WO | 2016097387 A1 | 6/2016 |
| WO | 2017042746 A1 | 3/2017 |
| WO | 2017108824 A1 | 6/2017 |
| WO | 2017109692 A1 | 6/2017 |

OTHER PUBLICATIONS

Reis et al., "Hair Cosmetics: An Overview." International Journal of Trichology Jan.-Mar. 2015; 7(1): 2-15. (Year: 2015).*

* cited by examiner

*Primary Examiner* — Walter E Webb

(57) ABSTRACT

An oil-in-water emulsion and a method of preparing the oil-in-water emulsion. The oil-in-water emulsion includes a siloxane mixture, a natural oil, an emulsifier and water.

18 Claims, No Drawings

OIL-IN-WATER EMULSION

CROSS-REFERENCE TO RELATED APPLICATIONS

This application is a U.S. National Phase application of PCT Application NO. PCT/CN2018/107847 filed on Sep. 27, 2018 the entire disclosure of which is incorporated by reference herein.

FIELD OF THE INVENTION

The present disclosure relates to an oil-in-water emulsion, and particularly to a mixed emulsion containing silicone oil and natural oil that can be used for hair care.

BACKGROUND OF THE INVENTION

Natural oil, especially vegetable oil, has been widely used in hair care products due to its mildness and unique efficacy. Vegetable oil can not only adhere to the hair surface, but also penetrate into the hair, lending it double-effect care. However, since vegetable oil contains a large amount of double bonds, it would be easily oxidized and become less effective if directly added to hair care products. Therefore, it is desirable to pre-emulsify vegetable oil before adding it to hair care products.

Currently, hair care products, typically shampoos, usually incorporate silicone oil for better smoothness. However, there is a big risk of stability of the formulation system when adding vegetable oil and silicone oil together due to their poor compatibility. In order to improve the stability of the mixed oil formulation, the vegetable oil and/or silicone oil to be used in mixed emulsions or hair care products are/is usually modified, or present only in a very small amount. Therefore, it is impossible to truly exert the synergetic efficacy of the two oils, which will affect the performance of products. CN104000749A, for example, discloses a scalp care solution in Example 2, which comprises 3 parts of siloxane emulsion (35 wt %), 2 parts of water-soluble vegetable oil, 5 parts of surfactant, 20 parts of denatured ethanol, and other ingredients, based on 100 parts by weight of the care solution.

In addition to hair care, a mixed emulsion containing silicone oil and vegetable oil is also used in cosmetics. For instance, EP0160430A discloses a mixed emulsion for treating dry, chapped skin in Example 8, comprising 17 parts of low viscosity silicone oils, 2.5 parts of vegetable oil and 1.5 parts of emulsifier, based on 100 parts by weight of the emulsion; WO2016097387A discloses a mixed emulsion which can improve the performance of cosmetics in Example 2, comprising 1.2 parts of emulsified amino-silicones, 10 parts of vegetable oil and 10 parts of emulsifier, based on 100 parts by weight of the emulsion. However, in order to prevent oil phase from separation, the silicone oils and vegetable oils are present in the above emulsions in a small amount.

There is also a prior art that silicone oil and vegetable oil, instead of pre-emulsified ones, are directly added during cosmetic preparation, but this method still fails to address the problem of stability and that vegetable oil is easily oxidized and become less effective. For instance, WO2009017866A1 discloses a cosmetic emulsion composition in Example 1, comprising 4 parts of low viscosity dimethicones, 0.4 parts of vegetable oils and 10.16 parts of emulsifiers, based on 100 parts by weight of the composition; WO2007133720A discloses an sunscreen emulsion in Example 15, comprising 15 parts of low viscosity silicone oils, 1 part of mineral oil, 0.5 parts of vegetable oil, 2 parts of emulsifier and 0.5 parts of thickener, based on 100 parts by weight of the emulsion; CN106109270A discloses a cosmetic emulsion composition in Example 4, comprising 20 parts of methicone, 45 parts of vegetable oil, 45 parts of emulsifier and 20 parts of thickener, based on 1000 parts by weight of the composition.

Therefore, there still needs to develop a technique for mixing silicone oil and vegetable oil to allow a stable emulsion that has high contents of silicone oil and vegetable oil and is beneficial for hair and scalp care.

SUMMARY OF THE INVENTION

The first aspect of the present disclosure provides an oil-in-water emulsion, wherein it has high contents of silicone oil and natural oil that are stably emulsified, the natural oil is encapsulated in the inner phase of the emulsion and can be effectively protected from oxidation to maximize its care efficacy, and surprisingly, the synergy between silicone compound, amino-functional silicone and natural oil provides double-effect care of the hair surface and inside as well as double care of the hair and scalp, especially reduced combing force and significantly improved hair softness.

As used herein, the term "oil-in-water emulsion" refers to a dispersion system where one liquid (oil phase) is dispersed in the form of droplets in the other liquid (aqueous phase). According to the present disclosure, the oil phase is present in the oil-in-water emulsion in an amount of more than 10 wt % (e.g. more than 15 wt % or 20 wt %), particularly more than 25 wt % (e.g. more than 30 wt %, 35 wt %, 40 wt %, 45 wt % or 50 wt %, or even more than 55 wt %, 60 wt % or 65 wt %, based on the total weight of the oil-in-water emulsion.

In the present disclosure, dynamic viscosity is measured at 25° C. according to DIN 53019, unless otherwise specified.

As used herein, the term "amine number" refers to, unless otherwise specified, the number of milligrams of hydrochloric acid and equivalent potassium hydroxide required to neutralize 1 g of the amino-functional silicone.

The oil-in-water emulsion comprises the following ingredients:
(a) a siloxane mixture, comprising (a1) a silicone compound having a dynamic viscosity at 25° C. of from 30,000 to 1,200,000 mPa·s and (a2) an amino-functional silicone having an amine number of from 1 to 50 mgKOH/g;
(b) natural oil;
(c) emulsifier; and
(d) water.

Ingredient (a1)

The silicone compound is a silicone without amino-functional groups, which may contain any number of $R_3SiO_{1/2}$, $R_2SiO_{2/2}$, $RSiO_{3/2}$ or $SiO_{4/2}$ siloxy units or a combination thereof, where R can be any monovalent organic group exclusive of amino-functional groups. These siloxy units can be combined in various ways to form a cyclic, linear or branched structure, preferably a linear structure. More preferably, the silicone compound has the following general formula:

$$R^1R^2{}_2SiO(R^2{}_2SiO)_m SiR^2{}_2R^1 \qquad \text{I}$$

where $R^2$ can be the same or different monovalent hydrocarbon groups having from 1 to 18 carbon atoms, for example from 1 to 6 carbon atoms, preferably methyl or ethyl, particularly preferably methyl;

$R^1$ can be the same or different $R^2$, hydroxyl groups or $C_1$-$C_6$ alkoxy groups, preferably methyl or ethyl, particularly preferably methyl;

m is preferably a number such that the silicone compound has a dynamic viscosity at 25° C. of from 40,000 to 1,000,000 mPa·s, preferably from 40,000 to 100,000 mPa·s.

Ingredient (a1) is suitably present in an amount of from 20 to 40 wt %, preferably from 24 to 36 wt %, for example 24 wt %, 30 wt %, and 36 wt %, based on the total weight of the emulsion.

Ingredient (a2)

The amino-functional silicone refers to the silicone mentioned above that is modified with one or more aminoalkyl functional groups, which preferably has the following general formula:

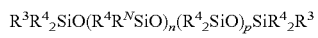    II where $R^4$ can be the same or different monovalent hydrocarbon groups having from 1 to 18 carbon atoms, for example from 1 to 6 carbon atoms, preferably methyl or ethyl, particularly preferably methyl;

$R^3$ can be the same or different $R^4$, hydroxyl groups or $C_1$-$C_6$ alkoxy groups, preferably methyl or ethyl, particularly preferably methyl;

$R^N$ is an amino group having the formula "—$R^a$—[$NR^b$—$R^c$—]$_x$$NR^b_2$" or a protonated form thereof, where $R^a$ is the same or different divalent hydrocarbon group having from 1 to 6 carbon atoms, preferably —$CH_2CH_2CH_2$— or —$CH_2CH(CH_3)$—$CH_2$—; $R^b$ can be the same or different H or monovalent hydrocarbon groups having from 1 to 4 carbon atoms, preferably H; $R^c$ can be the same or different divalent hydrocarbon groups having from 1 to 6 carbon atoms, preferably —$CH_2CH_2$—; x is preferably 0 or 1;

the sum of n+p is a number such that the amino-functional silicone compound has a dynamic viscosity at 25° C. of from 400 to 10,000 mPa·s, preferably from 2,000 to 6,000 mPa·s;

n is preferably a number such that the amino-functional silicone compound has an amine number of from 5 to 40 mgKOH/g, particularly from 5 to 10 mgKOH/g;

Ingredient (a2) is suitably present in an amount of from 5 to 15 wt %, for example 5 wt %, 10 wt %, and 15 wt %, based on the total weight of the emulsion.

To ensure the stability of emulsion and beneficial effects of hair care, the suitable mass ratio of ingredient (a1) to ingredient (a2) in ingredient (a) ranges from 1:1 to 10:1, preferably from 2:1 to 6:1, for example 4:1.

In certain embodiments, ingredient (a) is a mixture of a polydimethylsiloxane having a dynamic viscosity at 25° C. of from 40,000 to 70,000 mPa·s and a polydimethylsiloxane with aminoalkyl groups having a dynamic viscosity at 25° C. of from 2,000 to 6,000 mPa·s, mixed at a mass ratio of 4:1.

According to the present disclosure, ingredient (a) can be present in the oil-in-water emulsion in an amount of up to 60 wt %, for example from 20 to 60 wt % (e.g. 40 wt %, 50 wt % or 60 wt %), based on the total weight of the emulsion.

Ingredient (b)

The natural oil refers to oils directly extracted from animals, vegetables, seeds and nuts, and does not include oils extracted from petroleum or petroleum based oils. Examples of suitable natural oils include neatfoot oil, tallow, sheep fat, lard, horse fat, fish oil, almond oil, apricot oil, avocado oil, walnut oil, castor oil, corn oil, oat oil, cottonseed oil, rapeseed oil, linseed oil, grape seed oil, pomegranate seed oil, citrus seed oil, wheat germ oil, cashew nut oil, pine nut oil, macadamia nut oil, moroccanoil, peanut oil, soybean oil, sesame oil, sunflower oil, safflower oil, tea tree oil, rice bran oil, palm oil, palm kernel oil, coconut oil, olive oil, jojoba oil, argan oil, black cumin oil, bearberry oil, calophyllum oil, shea butter, or a combination thereof, but are not limited thereto. The natural oil is preferably that derived from vegetables, seeds or nuts.

The suitable mass ratio of ingredient (b) to ingredient (a) is 1:(1-8), for example 1:2 or 1:4 to obtain excellent combability, and preferably 1:(2-8) to ensure good softness at the same time. The suitable mass ratio of ingredient (b) to ingredient (a1) is 5:(4-32), for example 5:4, 5:8, 5:16 or 5:32, preferably 5:(8-32). The suitable mass ratio of ingredient (b) to ingredient (a2) is 5:(1-8), for example 5:1, 5:2, 5:4 or 5:8, preferably 5:(2-8).

According to the present disclosure, ingredient (b) can be present in the oil-in-water emulsion in an amount of up to 25 wt %, for example from 5 to 25 wt % (e.g. 5 wt %, 10 wt %, 15 wt %, 20 wt % or 25 wt %), preferably from 5 to 20 wt %. Ingredients (a) and (b) can be present in an total amount of up to 70 wt %, for example from 20 to 70 wt % (e.g. from 25 to 70 wt %, from 40 to 70 wt %), based on the total weight of the emulsion.

Ingredient (c)

The emulsifier can generally be a nonionic, cationic, anionic or amphoteric surfactant or a combination thereof, preferably one or more nonionic surfactants.

Typical nonionic surfactants include polyoxyethylene alkyl ethers, polyoxyethylene alkyl esters, polyoxyethylene sorbitol ethers, and copolymers of ethylene oxide and propylene oxide, preferably polyoxyethylene alkyl ethers and polyoxyethylene alkyl esters. Suitable polyoxyethylene alkyl ethers can be exemplified by polyoxyethylene ethers of $C_8$-$C_{16}$, such as $C_{10}$, $C_{11}$ or $C_{13}$ fatty alcohols, having from 3 to 50 EO units. Suitable polyoxyethylene alkyl esters can be exemplified by polyoxyethylene esters of $C_{16}$-$C_{18}$, such as $C_{18}$ fatty acids, having from 2 to 120 EO units.

The emulsifier preferably comprises at least three polyoxyethylene alkyl ethers or esters, in particular at least one polyoxyethylene alkyl ether or ester having an HLB value of from 5 to 10 and at least two polyoxyethylene alkyl ethers or esters having an HLB value of from 10 to 20, and the mixture thereof preferably has an HLB value of from 12 to 16, which can be evaluated by the following formula:

$$HLB_{MIX}=HLB_aW_a+HLB_bW_b+\ldots+HLB_nW_n$$

where $HLB_a$, $HLB_b$, and $HLB_n$ are the HLB values of polyoxyethylene alkyl ethers or esters a, b and n, respectively;

$W_a$, $W_b$ and $W_n$ are the mass percentages of polyoxyethylene alkyl ethers or esters a, b and n, respectively;

$HLB_{MIX}$ is the HLB value of the mixture.

In certain embodiments, the emulsifier is a mixture of one polyoxyethylene alkyl ether or ester having an HLB value of from 5 to 10 and two polyoxyethylene alkyl ethers or esters having an HLB value of from 10 to 20, for example, a mixture of Trideceth-3, Trideceth-10 and Trideceth-12, which has an HLB value of from 12 to 16.

According to the present disclosure, ingredient (c) can be present in the oil-in-water emulsion in an amount varying with the type of surfactant, and is generally from 20 to 30 wt % based on the total weight of the silicone mixture and natural oil. Surprisingly, the amount of emulsifier can be reduced to less than 15 wt %, such as from 10 to 15 wt %, based on the total weight of the silicone mixture and natural oil, while the silicone oil and natural oil are stably emulsified at high contents due to the synergy between one polyoxyethylene alkyl ether or ester having an HLB value of from 5 to 10 and two polyoxyethylene alkyl ethers or esters having an HLB value of from 10 to 20.

Other Optional Ingredients

According to the present disclosure, the oil-in-water emulsion can further include, as needed, other ingredients besides the above ones, such as a thickener, a pH adjuster, an antioxidant, a preservative and a moisturizer, but not limited thereto.

Any of the other optional ingredients mentioned above can be present in an amount of less than 10 wt %, preferably less than 5 wt %, for example less than 4 wt %, less than 3 wt %, less than 2 wt %, less than 1 wt %, less than 0.5 wt %, less than 0.2 wt %, or even less than 0.1 wt %, based on the total weight of the emulsion.

According to the present disclosure, the oil-in-water emulsion has a dynamic viscosity at 25° C. of from 1,000 to 20,000 mPa·s, for example, from 1,000 to 3,000 mPa·s, from 3,000 to 5,000 mPa·s, from 5,000 to 7,000 mPa·s, from 7,000 to 10,000. mPa·s, from 11,000 to 13,000 mPa·s, from 13,000 to 15,000 mPa·s, from 15,000 to 17,000 mPa·s, and from 17,000 to 20,000 mPa·s.

The second aspect of the present disclosure also provides a method for preparing the oil-in-water emulsion of the first aspect, which comprises the following steps of:
1) mixing the siloxane mixture with the natural oil to obtain a mixed oil;
2) mixing the emulsifier and the mixed oil to obtain a paste;
3) adding water to the paste and homogenizing to obtain the product.

The mixing operations in steps 1) and 2) can be carried out by any means known in the art, for example, by simple stirring at an unspecific speed as long as the ingredients are uniformly mixed.

In step 3), it is preferred to add water to the paste in several times, for example, more than 4 times, such as 5 or 6 times. The speed for homogenization can be arbitrary as long as the siloxane mixture and natural oil can be completely emulsified without oil separation.

The third aspect of the present disclosure provides use of the oil-in-water emulsion of the first aspect in personal care products.

The oil-in-water emulsion is used primarily as a conditioning ingredient in personal care products, including hair care and skin care products, preferably hair care products, more preferably rinse-off hair care products, such as shampoos and conditioners.

The fourth aspect of the present disclosure provides a rinse-off hair care product comprising the oil-in-water emulsion of the first aspect.

The dosage of the oil-in-water emulsion can be adjusted to individual needs, generally in an amount of from 1 to 10 wt %, for example, from 2 to 5 wt % (e.g. 3 wt %), of the total weight of the rinse-off hair care product.

DETAILED DESCRIPTION OF THE PREFERRED EMBODIMENTS

The present invention is further illustrated by the following examples, but is not limited to the scope thereof. Any experimental methods with no conditions specified in the following examples are selected according to the conventional methods and conditions, or product specifications.

1. Particle Size Test

According to the present invention, the particle size of the oil-in-water emulsion is characterized with a Malvern Zetasizer Nano ZS90 nanoparticle size analyzer. Prior to testing, the emulsion is diluted with deionized water to a suitable concentration, e.g. 0.5 wt %. The particle size of the emulsion is evaluated using median diameter ($D_{50}$).

2. Emulsion Stability Test

After the emulsion has been placed in an oven at 48° C. for two months, if no stratification is visible and all indicators (appearance, pH, viscosity, solid content, particle size, etc.) do not change significantly, it is regarded as stable.

3. Formulation of Shampoos

A shampoo formulated according to Table 1 was used to test the hair care efficacy of the oil-in-water emulsion of the present invention.

TABLE 1

| Ingredients | Content (wt %) |
|---|---|
| Sodium laureth sulfate | 14 |
| Cocamidopropyl betaine | 6.6 |
| Glycol distearate | 1 |
| Cocamide MEA | 0.5 |
| Cetearyl alcohol | 0.5 |
| Guar hydroxypropyltrimonium chloride | 0.2 |
| Polyquaternium-10 | 0.3 |
| Fragrance | 0.4 |
| Citric acid | 0.02 |
| Triethanolamine | 0.02 |
| NaCl | 0.4 |
| Preservative | 0.1 |
| Oil-in-water emulsion | 3.0 |
| Deionized water | q.s. to 100 |

4. Combing Force Test

According to the invention, the combing force is determined on an Instron 3365 tensile strength tester at 25±2° C. and 60±10% relative humidity. Each hair tress (weight 10 g, length 20 cm) needs to be measured continuously at least 11 times, where 5 groups of measurement data will be selected and averaged, in the following steps of:
1) placing an air dried hair tress as a blank on the tester fixture, and measuring its dry combing force $F_{dry(blank)}$;
2) completely wetting the hair tress with water, repeatedly rinsing 6 times, and removing the moisture from the tress;
3) taking 0.7 mL of shampoo for each hair tress and evenly applying thereon, washing the tress for 30 seconds and letting stand for another 30 seconds before rinsing 6 times with 35° C. warm water, and removing the moisture from the tress.
4) repeating step 3), gently detangling the hair with a wide-toothed comb, and hanging it on a hair rack for use;
5) placing the air dried hair tress in step 4) on the tester, measuring the dry combing force of the treated sample $F_{dry(sample)}$ and calculating the combing force reduction in form of percentage as $\Delta F_{dry}/\% = (F_{dry(blank)} - F_{dry(sample)})/F_{dry(blank)} *100\%$.

5. Softness Evaluation

The air dried hair tress in the above step 4) is hung, and touched by a 35-person test panel to evaluate its softness. The scoring rules are as follows: 0=fair, 1=good, 2=very good. The final result is the total score. The higher the score, the better the softness.

Listed in Table 2, the ingredients used in individual Examples and Comparative Examples are all commercially available, with detailed information as follows:

MULTISO 13/30, an iso-tridecanol polyoxyethylene ether with 3 EO units, having an HLB value of 7.9, supplied by Sasol Limited.

MULTISO 13/109, an aqueous solution of an iso-tridecanol polyoxyethylene ether with 10 EO units, having an active ingredient content of 90 wt % and an HLB value of 13.7, supplied by Sasol Limited.

MULTISO 13/120, an iso-tridecanol polyoxyethylene ether with 12 EO units, having an HLB value of 14.5, supplied by Sasol Limited.

BELSIL® DM60000, a polydimethylsiloxane, having a dynamic viscosity of about 60,000 mPa·s measured at 25° C. according to DIN 53019, supplied by Wacker Chemicals.

WACKER® AMINFLUID 6002, an aminoalkyl functional polydimethylsiloxane with an amine number of 6.7 mgKOH/g, having a dynamic viscosity of about 4,000 mPa·s measured at 25° C. according to DIN 53019, supplied by Wacker Chemicals.

Microcare IT, a liquid preservative with methylchloroisothiazolinone (1.1 wt %) and methylisothiazolinone (0.4 wt %) as active ingredients, supplied by Thor Chemicals.

Unless otherwise specified, "wt %" hereinafter is based on the total weight of the oil-in-water emulsion.

Examples 1-5

According to Table 2, the polydimethylsiloxane, the polydimethylsiloxane with aminoalkyl groups, and the natural oil were stirred and mixed uniformly, and the emulsifier was added to the resulting mixed oil, followed by stirring to obtain a paste, then 3.60 wt %, 5.61 wt %, 7.00 wt %, 12.00 wt % and 15.00 wt % water was added and homogenized sequentially to obtain the product. The resulting oil-in-water emulsions have a dynamic viscosity at 25° C. of from 3,000 to 10,000 mPa·s.

Comparative Examples 1-5

The preparation method of Comparative Examples 1-5 was basically the same as that of Examples 1-5 except that the natural oil in Comparative Example 1 was added after the emulsification of the polydimethylsiloxane and the polydimethylsiloxane with aminoalkyl groups; no natural oil was added to Comparative Example 2; no polydimethylsiloxane with aminoalkyl groups was added to Comparative Example 3; no polydimethylsiloxane was added to Comparative Example 4; no polydimethylsiloxane and polydimethylsiloxane with aminoalkyl groups were added to Comparative Example 5.

Table 3 lists the test results of particle size, stability and the combing force reduction in percentage as $\Delta F_{dry}$ for each of the Examples and Comparative Examples. In the same emulsifier system, the oil-in-water emulsions of Examples 1-5 are stable; the oil-in-water emulsion of Comparative Example 1 was not measured in terms of stability because the natural oil remained in a separated state since it was added after the emulsification of siloxane mixture; the oil-in-water emulsion of Comparative Example 4 containing the polydimethylsiloxane with aminoalkyl groups and natural oil, and that of Comparative Example 5 only containing the natural oil are unstable (compared with Example 2). A comparison between Example 1 and Comparative Example 2 shows that when a portion of the siloxane mixture is replaced with natural oil at the same oil phase mass, the resulting oil-in-water emulsion still has a comparable $\Delta F_{dry}$; the oil-in-water emulsions of Examples 2-4 further incorporate more natural oil in the oil phase, while $\Delta F_{dry}$ does not decrease significantly, which means it can still offer a good effect on reducing dry combing force. It is also remarkable that the natural oil that is not pre-emulsified and directly added to the shampoo is not as effective as the pre-emulsified one in reducing the dry combing force (comparing Example 2 and Comparative Example 1).

Table 4 shows the softness evaluation results of Examples 2-3 and Comparative Examples 2-3. In general, silicone oil is much more effective than natural oil in improving hair softness. However, at the same oil phase mass, the oil-in-water emulsion of Comparative Example 2 without natural oil and that of Comparative Example 3 without polydimethylsiloxane with aminoalkyl groups are much less softer than Examples 2-3 because natural oil, polydimethylsiloxane and polydimethylsiloxane with aminoalkyl group produce a synergy effect.

TABLE 2

| Ingredients (wt %) | Ex. 1 | Ex. 2 | Ex. 3 | Ex. 4 | Ex. 5 | C. Ex. 1 | C. Ex. 2 | C. Ex. 3 | C. Ex. 4 | C. Ex. 5 |
|---|---|---|---|---|---|---|---|---|---|---|
| MULTISO 13/30 | 0.70 | 0.70 | 0.70 | 0.70 | 0.70 | 0.70 | 0.70 | 0.70 | 0.70 | 0.70 |
| MULTISO 13/109 | 4.23 | 4.23 | 4.23 | 4.23 | 4.23 | 4.23 | 4.23 | 4.23 | 4.23 | 4.23 |
| MULTISO 13/120 | 2.10 | 2.10 | 2.10 | 2.10 | 2.10 | 2.10 | 2.10 | 2.10 | 2.10 | 2.10 |
| BELSIL® DM60000 | 35.56 | 32.00 | 26.66 | 20.00 | 32.00 | 32.00 | 40.00 | 40.00 | / | / |
| WACKER® AMINFLUID 6002 | 8.89 | 8.00 | 6.67 | 5.00 | 8.00 | 8.00 | 10.00 | / | 8.00 | / |
| Argan Oil | 5.56 | 10.00 | 16.67 | 25.00 | / | 10.00 | / | 10.00 | 10.00 | 10.00 |
| Macadamia oil | / | / | / | / | 10.00 | / | / | / | / | / |
| Water | 42.86 | 42.87 | 42.87 | 42.87 | 42.87 | 42.87 | 42.87 | 42.87 | 42.87 | 42.87 |
| Microcare IT | 0.10 | 0.10 | 0.10 | 0.10 | 0.10 | 0.10 | 0.10 | 0.10 | 0.10 | 0.10 |

TABLE 3

| Indicator | Ex. 1 | Ex. 2 | Ex. 3 | Ex. 4 | Ex. 5 | C. Ex. 1 | C. Ex. 2 | C. Ex. 3 | C. Ex. 4 | C. Ex. 5 |
|---|---|---|---|---|---|---|---|---|---|---|
| Particle size (nm) | 220 | 230 | 190 | 280 | 240 | n/a | 200 | 230 | n/a | n/a |
| Stability: | Stable | Stable | Stable | Stable | Stable | n/a | Stable | Stable | Unstable | Unstable |
| $\Delta F_{dry}/\%$ | 63 | 59 | 61 | 59 | n/a | 51 | 65 | 50 | n/a | n/a |

TABLE 4

| Indicator | Ex. 2 | Ex. 3 | C. Ex. 2 | C. Ex. 3 |
|---|---|---|---|---|
| Softness/score | 54 | 38 | 27 | 27 |

What is claimed is:

1. An oil-in-water emulsion comprising:
(a) a siloxane mixture, comprising (a1) a silicone compound having a dynamic viscosity at 25° C. of from 30,000 to 1,200,000 mPa·s and (a2) an amino-functional silicone having an amine number of from 1 to 50 mgKOH/g;
(b) natural oil;
(c) emulsifier; and
(d) water;
wherein ingredient (a1) is of the following formula:

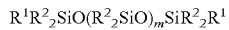
$R^1R^2{}_2SiO(R^2{}_2SiO)_mSiR^2{}_2R^1$ wherein $R^2$ is, identically or differently on each occurrence, a monovalent hydrocarbon group having from 1 to 18 carbon atoms;
wherein $R^1$ is, identically or differently on each occurrence, $R^2$, hydroxyl group or a $C_1$-$C_6$ alkoxy group;
wherein the mass ratio of ingredient (b) to ingredient (a1) is 5:(4-32); and
wherein the mass ratio of ingredient (b) to ingredient (a2) is 5:(1-8).

2. The oil-in-water emulsion of claim 1, wherein the mass ratio of ingredient (b) to ingredient (a) is 1:(1-8).

3. The oil-in-water emulsion of claim 2, wherein the mass ratio of ingredient (b) to ingredient (a) is 1:(2-8).

4. The oil-in-water emulsion of any one of claim 1, wherein the ingredient (b) is present in an amount of from 5 to 25 wt % based on the total weight of the emulsion.

5. The oil-in-water emulsion of any one of claim 1, wherein the ingredient (a) is present in an amount of from 20 to 60 wt % based on the total weight of the emulsion.

6. The oil-in-water emulsion of any one of claim 1, wherein the ingredients (b) and (a) are present in a total amount of from 40 to 70 wt % based on the total weight of the emulsion.

7. The oil-in-water emulsion of any one of claim 1, wherein the ingredient (b) is an oil derived from vegetables, seeds or nuts.

8. The oil-in-water emulsion of any one of claim 1, wherein the ingredient (c) comprises one polyoxyethylene alkyl ether or ester having an HLB value of from 5 to 10 and two polyoxyethylene alkyl ethers or esters having an HLB value of from 10 to 20.

9. The oil-in-water emulsion of claim 8, wherein the ingredient (c) has an HLB value of from 12 to 16.

10. The oil-in-water emulsion of claim 8, wherein the ingredient (c) is present in an amount of less than 15 wt % based on the total weight of the silicone mixture and natural oil.

11. The oil-in-water emulsion of any one of claim 1, wherein the ingredient (a1) has a dynamic viscosity at 25° C. of from 40,000 to 100,000 mPa·s.

12. The oil-in-water emulsion of any one of claim 1, wherein the ingredient (a2) has an amine number of from 5 to 10 mgKOH/g.

13. A method for preparing the oil-in-water emulsion, comprising:
providing an oil-in-water emulsion comprising (a) a siloxane mixture, comprising (a1) a silicone compound having a dynamic viscosity at 25° C. of from 30,000 to 1,200,000 mPa·s and (a2) an amino-functional silicone having an amine number of from 1 to 50 mgKOH/g, (b) natural oil, (c) emulsifier, and (d) water, wherein ingredient (a1) is of the formula: $R^1R^2{}_2SiO(R^{22}SiO)_mSiR^2{}_2R^1$, wherein where $R^2$ is, identically or differently on each occurrence, a monovalent hydrocarbon group having from 1 to 18 carbon atoms, wherein $R^1$ is, identically or differently on each occurrence, $R^2$, hydroxyl group or a $C_1$-$C_6$ alkoxy group; and
wherein the mass ratio of ingredient (b) to ingredient (a1) is 5:(4-32);
wherein the mass ratio of ingredient (b) to ingredient (a2) is 5:(1-8); and
wherein the oil-in-water emulsion has a particle size of less than 500 nm.

14. The method for preparing an oil-in-water emulsion of claim 13, further comprising the following steps of:
1) Mixing the siloxane mixture with the natural oil to obtain a mixed oil;
2) Mixing the emulsifier and the mixed oil to obtain a paste; and
3) adding water to the paste and homogenizing to obtain the product.

15. The method for preparing an oil-in-water emulsion of claim 13, wherein the oil-in-water emulsion is used in personal care products.

16. The method for preparing an oil-in-water emulsion of claim 15, wherein the personal care products are rinse-off hair care products.

17. The oil-in-water emulsion of claim 1, wherein the oil-in-water emulsion is used in personal care products.

18. The oil-in-water emulsion of claim 17, wherein the personal care products are rinse-off hair care products.

* * * * *